United States Patent [19]

Mizuno et al.

[11] Patent Number: 5,348,649
[45] Date of Patent: Sep. 20, 1994

[54] APPARATUS FOR MEASURING GLYCOHEMOGLOBIN

[75] Inventors: Masako Mizuno, Mito; Kenji Tochigi, Tokyo; Yutaka Misawa, Katsuta, all of Japan

[73] Assignee: Hitachi, Ltd., Tokyo, Japan

[21] Appl. No.: 59,931

[22] Filed: May 11, 1993

Related U.S. Application Data

[63] Continuation of Ser. No. 733,808, Jul. 22, 1991, abandoned.

[30] Foreign Application Priority Data

Jul. 20, 1990 [JP] Japan .................................. 2-192423

[51] Int. Cl.$^5$ .............................................. B01D 15/08
[52] U.S. Cl. .............................. 210/198.2; 210/502.1; 210/635; 210/656; 422/70
[58] Field of Search ...................... 210/635, 656, 198.2, 210/502.1; 530/385; 422/70; 436/66, 67, 161

[56] References Cited

U.S. PATENT DOCUMENTS

| 3,959,080 | 5/1976 | Orth ...................... 436/519 |
| 4,029,583 | 6/1977 | Ho Chang ................ 210/502.1 |
| 4,371,374 | 2/1983 | Cerami ...................... 436/87 |
| 4,705,628 | 11/1987 | Yamamoto ............... 210/502.1 |
| 4,810,391 | 3/1989 | Bruegger ................ 210/198.2 |
| 4,879,039 | 11/1989 | Takahashi ................. 210/656 |
| 4,913,812 | 4/1990 | Moriguchi ................ 210/635 |
| 5,002,613 | 3/1991 | Carobbi .................. 127/46.2 |
| 5,019,269 | 5/1991 | Letourneur ............... 210/635 |
| 5,153,166 | 10/1992 | Jain ........................ 502/402 |

FOREIGN PATENT DOCUMENTS

| 63-36143 | 2/1988 | Japan ................ 210/198.2 |
| 63-75558 | 4/1988 | Japan ................ 210/198.2 |
| 63-298063 | 12/1988 | Japan ................ 210/198.2 |
| 63-298064 | 12/1988 | Japan ................ 210/198.2 |
| 197857 | 4/1989 | Japan ................ 210/198.2 |
| 1143957 | 6/1989 | Japan ................ 210/198.2 |
| 2259467 | 10/1990 | Japan ................ 210/198.2 |
| 434364 | 2/1992 | Japan ................ 210/198.2 |

OTHER PUBLICATIONS

Nathan, Clin. Chem. 28/3, Rapid Method of Eliminating Labile Glycosylated Hemoglobin, 1982, pp. 512–515.

Nathan, Clin. Chem. 27/7, Labile Glycosylated Hemoglobin Contributes to Hemoglobin A, pp. 1261–1263, (1981).

*Primary Examiner*—Ernest G. Therkorn
*Attorney, Agent, or Firm*—Antonelli, Terry, Stout & Kraus

[57] ABSTRACT

In separation column 23 is packed a filler consisting of an inorganic or organic porous substance having carboxyalkyl group and dihydroxyboronyl group. Thus, the separation column 23 can concurrently perform the procedure of separating glycohemoglobin, hemoglobin and hemoglobin derivatives in blood and the procedure of decomposing labile-type hemoglobin in blood into glucose and hemoglobin to remove the labile-type hemoglobin, when a diluted blood sample on sample table 19 along with eluents 8 to 10 is transferred to the separation column 23. Then, stable-type hemoglobin in the eluate from the separation column 23 is measured by UV-VIS detector 25.

6 Claims, 6 Drawing Sheets

APPARATUS FOR MEASURING GLYCOHEMOGLOBIN

This application is a continuation application of application Ser. No. 733,808, filed Jul. 22, 1991, now abandoned.

BACKGROUND OF THE INVENTION

1. Field of the Invention

The present invention relates to a method for measuring stable-type hemoglobin in blood and an apparatus for measuring the same.

2. Description of the Prior Art

After blood sugar enters into red blood cells depending on its concentration, the sugar is bound with hemoglobin to form glycohemoglobin. It is indicated that the concentration of stable-type A1c (referred to as stable-A1c or abbreviated as $s-A_{1c}$ hereinafter) among various types of glycohemoglobin reflects the average blood glucose level for the latest 1 to 3 months.

$A_{1c}$ is composed of stable-type $A_{1c}$ ($s-A_{1c}$) and labile-type $A_{1c}$ (labile-$A_{1c}$; $l-A_{1c}$). Of the two, $s-A_{1c}$ exhibits good correlation with the blood glucose level for the latest 1 to 3 months. It is suggested that $l-A_{1c}$ is about 10 to 15% of the total $A_{1c}$ in a hungry healthy adult. The $l-A_{1c}$ is formed by the reversible binding of N terminus of β-chain hemoglobin and a reducing terminus of glucose through a Schiff base, and is generated and decomposed in a relatively short period. In diabetic patients, the $l-A_{1c}$ content is therefore higher than in healthy adults, sometimes amounting up to 10 to 20% of the total $A_{1c}$. It is also higher after meal than in hunger, and is remarkably influenced by the state when blood is collected.

Alternatively, $s-A_{1c}$ is gradually generated from $l-A_{1c}$, continuously and irreversibly. It is suggested that $s-A_{1c}$ reflects very well the blood glucose level for the latest 1 to 3 months.

Hence, it is preferable that $s-A_{1c}$ is separated and measured singly. However, the two are extremely analogous in structure, so they are considerably hard to separate by liquid chromatography.

The method of measuring only $s-A_{1c}$ includes two methods; (1) a method of separating and measuring $s-A_{1c}$ and $l-A_{1c}$ on a separation column by chromatography; and (2) a method of pretreating and removing $l-A_{1c}$.

In the method for separating $l-A_{1c}$ and $s-A_{1c}$ on a separation column, a long, highly preparative separation column is employed for improving preparative performance. The method has a characteristic property in that hemoglobin is hardly denatured compared with the method to remove $l-A_{1c}$ by its pretreatment (see for example, Gazette of Japanese Patent Laid-open No.75558/1988).

On the other hand, the method to chemically remove $l-A_{1c}$ by its pretreatment includes the method to incubate red blood cells in physiological saline or a buffer containing semicarbazide and aniline (D. M. Nathan, Clin. Chem., 27, 1261 (1981); D. M. Nathan, et al., Clin. Chem., 28,512 (1982)). Such method focuses on the evidence that the temporary binding of $l-A_{1c}$, i.e. the binding through a Schiff base, readily decomposes.

It has been proposed also a method comprising adding a commercially available reagent to blood for removing $l-A_{1c}$, and subsequently heating the blood at about 50° C. for 1 to 2 minutes, thereby removing $l-A_{1c}$ (see for example, Gazette of Japanese Patent Laid-open No. 36143/1988; Gazette of Japanese Patent Laid-open No. 97857/1989).

Of the prior art techniques, however, the complete separation of $l-A_{1c}$ and $s-A_{1c}$ according to the method of separating $l-A_{1c}$ and $s-A_{1c}$ on a separation column requires an analytical time as long as about 10 to 60 minutes per one sample. Therefore, it is nearly impossible to treat a large number of samples. Because such column is so long that it requires a large amount of fillers, the method has disadvantages that the column costs high and that the apparatus therefor should be bulky.

According to the method of removing $l-A_{1c}$ by its pretreatment, the pretreatment per se is complex and requires 30 minutes to four hours. The method has a problem also in treating many samples.

Further, the method of heat treatment has a problem that analysis may eventually be impossible in case that the protein in blood is denatured resulting in the occurrence of precipitation, which may clog pipes and filters.

SUMMARY OF THE INVENTION

It is the object of the present invention to provide a method for measuring glycohemoglobin and an apparatus for measuring the same, characterized in that stable-type $A_{1c}$ ($s-A_{1c}$) can be separated from other hemoglobin components for a short period and that the clogging of pipes and filters can be prevented.

In order to achieve the above object, the measuring method of the present invention comprises effecting concurrently a process of separating glycohemoglobin, hemoglobin and hemoglobin derivatives in blood and a process of decomposing labile-type hemoglobin in the blood into glucose and hemoglobin, thereby removing the labile-type hemoglobin component, and measuring stable-type hemoglobin, by means of high-performance liquid chromatography.

The method for measuring glycohemoglobin in blood by high-performance chromatography in accordance with the present invention comprises passing eluents through a separation column packed with a filler consisting of an inorganic or organic porous substance having carboxyalkyl group and dihydroxyboronyl group, thereby decomposing and removing labile-type hemoglobin in the blood, and subsequently measuring stable-type glycohemoglobin in the blood.

The method for measuring glycohemoglobin in blood by high-performance chromatography in accordance with the present invention comprises passing eluents through a separation column wherein a filler consisting of an inorganic or organic porous substance having carboxyalkyl group and a filler consisting of an inorganic or organic porous substance having dihydroxyboronyl group are mixed together, thereby decomposing and removing labile-type hemoglobin in the blood, and subsequently measuring stable-type glycohemoglobin in the blood.

The method for measuring glycohemoglobin in blood by high-performance chromatography in accordance with the present invention comprises passing eluents between a type of fillers each consisting of an inorganic or organic porous substance having carboxyalkyl group and sequentially passing the eluents between another type of fillers each consisting of an inorganic or organic porous substance having dihydroxyboronyl group, or passing eluents in the eluting order reverse to the aforementioned order, thereby decomposing and removing labile-type hemoglobin in the blood, and subsequently measuring stable-type glycohemoglobin in the blood.

The present invention is an apparatus for measuring stable-type glycohemoglobin by high-performance liquid chromatography, comprising a separation column for separating glycohemoglobin in blood, a means for injecting a diluted blood sample into the separation column, a means for passing eluents into the separation column and a means for detecting stable-type hemoglobin in an eluate from the separation column, wherein the separation column is provided with the function for simultaneously carrying out the procedure of separating glycohemoglobin, hemoglobin and hemoglobin derivatives and the procedure of decomposing labile-type hemoglobin in the blood into glucose and hemoglobin so as to remove the labile-type hemoglobin.

The present invention is an apparatus for measuring stable-type glycohemoglobin by high-performance liquid chromatography, comprising a separation column for separating glycohemoglobin in blood, a means for injecting a diluted blood sample into the separation column, a means for passing eluents into the separation column and a means for detecting stable-type hemoglobin in an eluate from the separation column, wherein the separation column is packed with a filler consisting of an inorganic or organic porous substance having carboxyalkyl group and dihydroxyboronyl group.

The present invention is an apparatus for measuring stable-type glycohemoglobin by high-performance liquid chromatography, comprising a separation column for separating glycohemoglobin in blood, a means for injecting a diluted blood sample into the separation column, a means for passing eluents into the separation column and a means for detecting stable-type hemoglobin in an eluate from the separation column, wherein the separation column is packed with a filler produced by mixing a filler consisting of an inorganic or organic porous substance having carboxyalkyl group and a filler consisting of an inorganic or organic porous substance having dihydroxyboronyl group.

The present invention is an apparatus for measuring stable-type glycohemoglobin by high-performance liquid chromatography, comprising a separation column for separating glycohemoglobin in blood, a means for injecting a diluted blood sample into the separation column, a means for passing eluents into the separation column and a means for detecting stable-type hemoglobin in an eluate from the separation column, wherein a filler consisting of an inorganic or organic porous substance having carboxyalkyl group and a filler consisting of an inorganic or organic porous substance having dihydroxyboronyl group are separately packed in two layers in the separation column.

The present invention is an apparatus for measuring stable-type glycohemoglobin by high-performance liquid chromatography, comprising a separation column for separating glycohemoglobin in blood, a means for injecting a diluted blood sample into the separation column, a means for passing eluents into the separation column and a means for detecting stable-type hemoglobin in an eluate from the separation column, wherein the separation column is divided in two parts in the flow direction of eluents, one part being packed with a filler consisting of an inorganic or organic porous substance having carboxyalkyl group and the other part being packed with a filler consisting of an inorganic or organic porous substance having dihydroxyboronyl group.

Furthermore, the separation column of the present invention is packed with a filler consisting of an inorganic or organic porous substance, having carboxyalkyl group and dihydroxyboronyl group.

Still furthermore, the separation column of the present invention is packed with a filler produced by mixing a filler consisting of an inorganic or organic porous substance having carboxyalkyl group and a filler consisting of an inorganic or organic porous substance having dihydroxyboronyl group.

Further, the separation column of the present invention is produced by packing a filler consisting of an inorganic or organic porous substance having carboxyalkyl group and a filler consisting of an inorganic or organic porous substance having dihydroxyboronyl group, separately in two layers in the flow direction of eluents.

DETAILED DESCRIPTION OF THE INVENTION AND PREFERRED EMBODIMENTS

By using, as the separation column for analysis of glycohemoglobin, a separation column packed with a filler having carboxyalkyl group and dihydroxyboronyl group, the decomposition of l-$A_{1c}$ and the separation thereof into the individual components of hemoglobin (Hb) can be simultaneously carried out.

In case that glycohemoglobin (GHb) is separated into its components by high-performance liquid chromatography (HPLC), there is used, as the filler, a cation exchange resin of a weak acidity wherein carboxymethyl group is introduced into a hydrophilic substrate such as silicagel, methacrylate gel, vinyl alcohol gel and the like. By the ion exchange chromatography, Hb is separated into its individual components by utilizing the difference in the isoelectric points.

Alternatively, a filler having dihydroxyboronyl group is used in affinity chromatography. When an eluent is passed through a column packed with a filler having dihydroxyboronyl group, l-$A_{1c}$ is decomposed into HbA$_0$ and glucose. Because l-$A_{1c}$ is produced by binding of N-terminus of $\beta$-chain Hb with the reducing terminus of glucose, as shown in formula 1, it is extremely unstable. For that reason, the equilibrium moves to the right direction, and l-$A_{1c}$ decomposes into HbA$_0$.

As is shown in formula 2, glycohemoglobin in which sugar such as glucose is bound to Hb is separated from non-glycohemoglobin (Hb) by affinity chromatography, generally utilizing the specific reaction of dihydroxyboronyl group introduced into a solid phase with 1,2-cis-diol group. This reaction progresses at pH 8 or more.

(2)

Because the filler having dihydroxyboronyl group is used for the objective to decompose $l$-$A_{1c}$ into glucose and Hb, not for the separation of glycohemoglobin and non-glycohemoglobin, pH 8 or less is preferable, or pH 7 or less is more preferable.

At pH 8 or more, glycohemoglobin is specifically bound to the dihydroboronyl group, and is adsorbed onto the filler.

The isoelectric points of Hb and GHb are from 6.90 to 6.95. When Hb and GHb are separated from each other by ion exchange chromatography employing (carboxyalkyl group-introduced) weakly-acidic cation exchange resin, an eluent with a lower pH than the individual isoelectric points of Hb and GHb should be used. Accordingly, there is no chance that glycohemoglobin may be bound the dihydroxyboronyl group.

By using the filler having carboxyalkyl group and dihydroxyboronyl group, as has been described, s-$A_{1c}$ can be separated and measured with no influence of $l$-$A_{1c}$ variable due to physiological factors and diet.

As the separation column, there can be used a column packed with a filler having both of carboxyalkyl group and dihydroxyboronyl group.

On the other hand, after removing $l$-$A_{1c}$ on a column packed with a filler having dihydroxyboronyl group, Hb is separated into its individual components on a separation column sacked with a filler having carboxyalkyl group.

On the contrary, after Hb is separated into its individual components on a separation column packed with a filler having carboxyalkyl group, $l$-$A_{1c}$ can be removed on a column packed with a filler having a dihydroxyboronyl group.

Further, it may be used a column wherein a filler having dihydroxyboronyl group and a filler having carboxyalkyl group are mixed together and packed, or they are sequentially packed in layers.

According to the present method, the eluents which have conventionally been used for ion exchange chromatography can be used as they are. Hence, the examination of the elution conditions is not specifically required.

Since the removal of $l$-$A_{1c}$ is unnecessary because of the pretreatment, the analytical procedure is easy; and the time for analysis is shortened since the pretreatment is not required. The decomposition and degeneration of Hb and GHb do not occur, excluding $l$-$A_{1c}$.

Thus, following the separation method of glycohemoglobin employing such separation column in accordance with the present invention, stable-type $A_{1c}$ (s-$A_{1c}$) in blood can be analyzed rapidly, stably with good reproducibility and easily, with no influence of labile-type $A_{1c}$ ($l$-$A_{1c}$) which level varies depending on physiological factors.

EXAMPLES

The examples of the present invention will now be explained in drawings hereinafter.

As the filler of the present invention, there can be used the one wherein carboxyalkyl group and dihydroxyboronyl group are introduced into one particle. As a separation column, it may be used a column packed with a filler introduced with carboxyalkyl group concurrently with a filler introduced with dihydroxyboronyl group. As such column, furthermore, there may be used a column separately packed with a filler introduced with carboxyalkyl group and a filler introduced with dihydroxyboronyl group.

As the matrix (substrate) for introducing carboxyalkyl group and/or dihydroxyboronyl group, those matrices having conventionally been used for liquid chromatography can be used. However, those with intense mechanical strength, less non-specific proteinous adsorption (not too intense hydrophilicity) and chemical stability are preferable. As the matrix satisfying such requirements, hydrophilic, organic porous substances (cross-linked polymer) including methacrylate gel and vinyl alcohol gel can be used. Because a buffer of pH 7 or less is used as the eluent, inorganic porous substances such as silica gel can be used.

The method for introducing dihydroxyboronyl group into such matrices described above is illustrated in the following methods. Such matrices are reacted with epihalohydrin, bis-epoxide and the like, followed by the reaction with meta-aminophenyl boronic acid, whereby the introduction of dihydroxyboronyl group into the matrices is achieved. By introducing carboxyalkyl group into the hydroxyl group of a matrix by known methods and subsequently transforming the carboxyalkyl group into azide, which is then reacted with meta-aminophenyl boronic acid, the introduction of dihydroxyboronyl group into the matrix is achieved. By reacting bromcyane with the hydroxyl group of a matrix, followed by the reaction with oligopeptide, and reacting meta-aminophenyl boronic acid in the presence of carbodiimide, the introduction of dihydroxyboronyl group into the matrix is achieved.

The method for introducing carboxyalkyl group into the matrices includes a method of reacting halogenated acetic acid including monochloroacetic acid and monobromoacetic acid with the hydroxyl group of the matrices.

Preferably, the amount of carboxyalkyl group to be introduced is 0.1 to 1 meq (milli equivalent) per g.dry weight of a filler. Preferably, the amount of dihydroxyboronyl group to be introduced is 0.1 to 1 meq (milli equivalent) per g.dry weight of a filler.

The amount of dihydroxyboronyl group can be measured and determined, for example, by alkali titration under the condition of allowing a filler having dihydroxyboronyl group and sorbitol to be present in an aqueous solution (Japanese Chemical Society "New Experimental Chemistry Series (Shin-Jikken Kagaku Koza) (Analytical Chemistry I)", (1976), Maruzen, page 77). The amount of boric acid released by hydrogen peroxide treatment of a filler having dihydroxyboronyl group can be determined by the titration described above. The amount of boric acid may be determined by atomic absorption and emission spectral analysis as well. The amount of carboxyalkyl group can be determined by a conventionally known and commonly employed method of measuring the exchange capacity of carboxyl group.

As the filler having carboxyalkyl group, various fillers may be used, including those having carboxymethyl group, carboxyethyl group and the like. More preferably, a filler having carboxymethyl group may be used.

The form of the filler to be used in accordance with the present invention includes various forms such as spherical forms and crushed forms, but spherical forms are more preferable in order to yield high separation. The particle diameter is 1 to 200 $\mu$m, preferably 1 to 20 $\mu$m, and more preferably 1 to 10 $\mu$m.

The column of the present invention desirably is of a cylindrical form of an inner diameter of 1 to 10 mm and a length of 20 cm or less, preferably a cylindrical form of an inner diameter of 1 to 6 mm and a length of 1 to 10 cm.

As the method for packing a filler in a column, any conventionally known method may be used as long as it can afford the packing in uniform state and can control the filling rate. The filling rate can be regulated by the control of the pressure and the packing period.

The eluent may be an eluent commonly used for analysis of glycohemoglobin is analyzed by liquid chromatography, provided that the eluent is a buffer of pH 5.0 to 7.0. There are used, for example, buffers including sodium acetate, sodium phosphate, potassium phosphate and the like, or solutions containing salts such as sodium chloride, sodium sulfate and the like. Urea and guanidine may be added as well. Organic solvents such as acetonitrile, ethanol, methanol, mercaptoethanol and the like may be mixed therein.

The concentration and pH of an eluent composition including buffers, salts, urea, organic solvents and the like, are not necessarily constant for analysis of hemoglobin, glycohemoglobin and hemoglobin derivatives. They may be subjected to change for example by continuously gradient method or step-wise gradient method. The flow of an eluent to be transferred is not necessarily constant, and it can be modified continuously or in step-wise manner according to time course.

Glycohemoglobin, hemoglobin and hemoglobin derivatives, which are separated from the eluate by means of the separation column of the present invention, can be detected based on the measurement of visible ray at a wave length of 415 mm. When the pH and concentration of an eluent is subjected to change, the change in refractive index induces absorption. Thus, the visible ray at a wave length of 690 mm, at which the absorption of glycohemoglobin, hemoglobin and the like won't occur, may be used for the measurement for reference.

The present invention will now be explained in the examples hereinafter.

EXAMPLE 1

There was used a filler wherein carboxymethyl group and dihydroxyboronyl group were introduced as functional groups into methacrylate polymer as a matrix.

Table 1 shows the results of the measurement, in Example 1 and Comparative Example 1, of physical values and pressure loss of the filler. The filler of Example 1 is produced by introducing dihydroxyboronyl group into the filler having carboxymethyl group of Comparative Example 1. Example 1 is nearly equal to Comparative Example 1, in terms of particle diameter, specific surface area, and the amount of carboxymethyl group. That is, even if dihydroxyboronyl group is introduced, the particle diameter, the specific surface area and the amount of carboxymethyl group do not change so much.

These two fillers were packed separately in a stainless-steel column of an inner diameter of 4.6 mm and a length of 80 mm as a separation column. The packing was carried out following slurry method. 80 mM potassium phosphate of pH 6.20 was used as the slurry solvent and packing solvent. The packing solvent was eluted at a packing pressure of 150 kg/cm$^2$ for one hour.

TABLE 1

|  | Column size | Particle diameter ($\mu$m) | Specific surface area (m$^2$) |
| --- | --- | --- | --- |
| Example 1 | ⌀ 4.6 × 80 mm | 4.5 ± 0.8 | 20 |
| Comparative Example 1 | ⌀ 4.6 × 80 mm | 4.5 ± 0.8 | 18 |

|  | Carboxymethyl group (meq/g) | Dihydroxymethyl group (meq/g) | Pressure loss P 1) (kg/cm$^2$) |
| --- | --- | --- | --- |
| Example 1 | 0.30 | 0.18 | 98 |
| Comparative Example 1 | 0.28 | — | 95 |

1) Flow of eluent: 1.2 ml/min

As a sample, fresh blood from healthy adults was used, which had been collected after the addition of sodium ethylenediamine retracetate as an anti-coagulant. A commercially available hemolytic agent was added to the fresh blood for 200-fold dilution, and the resulting hemolytic solution was used as a sample.

As the eluents, monopotassium phosphate (KH$_2$PO$_4$) and dipotassium phosphate (K$_2$HPO$_4$) were used, after they were preliminarily dissolved in deionized water so as to be adjusted of their concentrations as follows.

A solution;
33 mM KH$_2$PO$_4$
7 mM K$_2$HPO$_4$
pH 6.2
B solution;
66 mM KH$_2$PO$_4$
14 mM K$_2$HPO$_4$
pH 6.2
C solution;
160 mM KH$_2$PO$_4$
40 mM K$_2$HPO$_4$
pH 6.1

As experimental systems, there were individually used an intelligent pump of HITACHI L-6200 type, an injector of a 10 -μl capacity, a detector of HITACHI L-4200 type UV-VIS, a data processor of HITACHI D-2500 type.

Measurement was effected at a column temperature of 25° C. and a detection wave length of 415 nm. The separation of individual components was according to the step-wise gradient method as shown in the following;

| | |
|---|---|
| First solution: A solution | 0–0.4 min |
| Second solution: A solution/B solution = 50/50 | 0.5–3.0 min |
| Third solution: C solution | 3.1–3.8 min |
| First solution: A solution | 3.9–7.0 min |
| Flow of eluent: 1.2 ml/min | |
| Injection volume of sample: 10 μl | |

Figure 1:
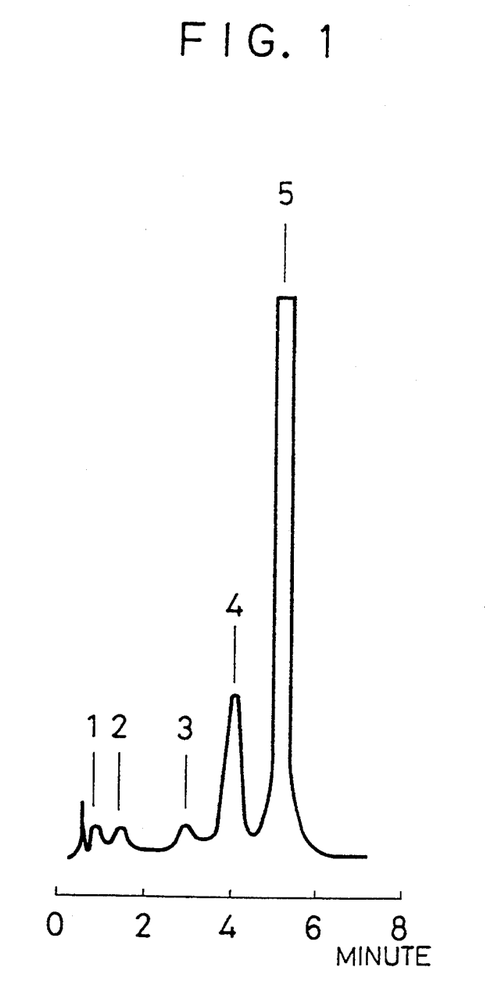
FIG. 1 shows the chromatogram obtained in Example 1.
Figure 2:
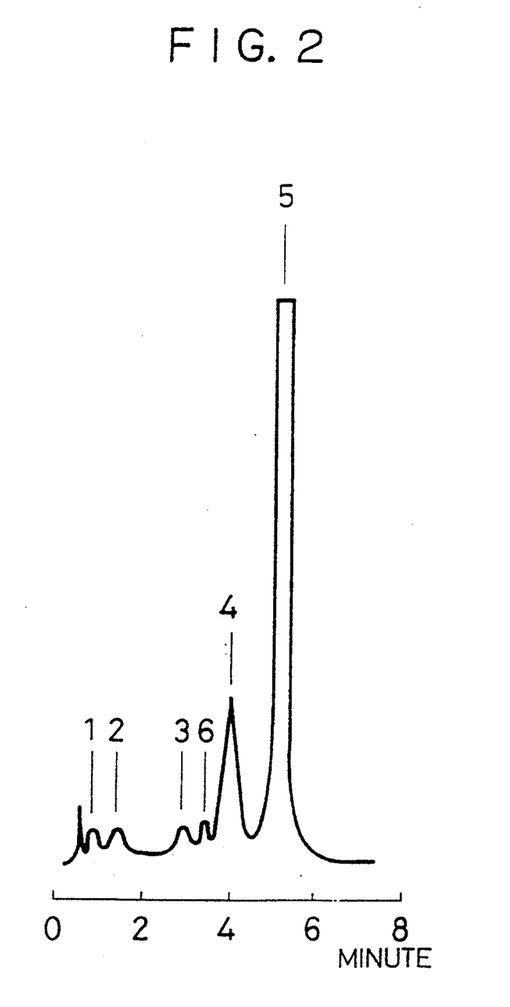
FIG. 2 shows the chromatogram obtained in Comparative Example 1.

Under the analytical conditions described hereinabove, the chromatogram obtained on the separation column of Example 1 and the chromatogram obtained on the separation column of Comparative Example 1 are shown in FIGS. 1 and 2, respectively.

In FIGS. 1 and 2, Peak 1 represents $A_{1a}$; Peak 2, $A_{1b}$; Peak 3, HbF; Peak 4, stable-type $A_{1c}$ (s-$A_{1c}$); Peak 5, HbAc; Peak 6, labile-type $A_{1c}$ (l-$A_{1c}$).

The individual peaks were identified as follows; various types of glycohemoglobin can be generated by incubation of blood with sugar derivatives, and the confirmation of peaks then enhanced enables the identification of the individual peaks.

Peak 1 ($A_{1c}$) was identified by the addition of fructose-1,6-diphosphate and glucose-6-phosphate, while Peak 2 ($A_{1a}$) was identified by the addition of pyruvic acid. Peak 6 is considered to be l-$A_{1c}$, because Peak 6 was distinctly enhanced when a sample was prepared and measured after glucose was added to blood for incubation, and because Peak 6 was decreased when a sample was prepared and measured, after glucose was added to blood for incubation and the blood was then incubated in physiological saline at 45° C. for four hours. On the other hand, Peak 4 may be regarded as s-$A_{1c}$ because Peak 4 did not increase or decrease even after the addition of glucose or the incubation in physiological saline. Peak 3 is considered to be HbF, because the peak exhibits the same performance as that of the principal components of navel blood.

In case of Comparative Example 1 in FIG. 2, Peak 6 representing l-$A_{1c}$ emerges. On the contrary, in case of using the separation column of Example 1, l-$A_{1c}$ is completely removed as shown in FIG. 1. The retention times of the individual components, i.e. $A_{1a}$, $A_{1b}$, HbF, s-$A_{1c}$ and HbA$_0$, are nearly equal on the separation columns of Example 1 and Comparative Example 1. The pressure losses of the columns at an eluent flow of 0.2 ml/min were almost equal, namely, 98 kg/cm$^2$ in Example 1 and 95 kg/cm$^2$ in Comparative Example 1.

According to the present Example, the removal (decomposition) of Hb and the separation thereof into the individual components can be carried out simultaneously, as has been described above, so that it is possible to shorten the treatment period for removal of l-$A_{1c}$, which has taken a time as long as 15 min to four hours in the prior art. Because l-$A_{1c}$ can be removed continuously within the system, such complex procedures as have been carried out conventionally are not required any more. As the time required for the decomposition of l-$A_{1c}$ is short, accurately measured values of s-$A_{1c}$ can be obtained without the generation or decomposition of GHb and HB involved in the removal process of l-$A_{1c}$.

According to the present Example, it is observed in FIG. 1 of Example 1 that the individual Hb components are fully separated on the separation column of Example 1. Consequently, the analytical time can be further shortened by the employment of a shorter column and the increase of an eluent volume.

EXAMPLE 2

Concerning Example 2 and Comparative Example 2, Table 2 shows the physical values and pressure loss of the fillers. The separation columns of Example 2 and Comparative Example 2 are produced by packing the fillers of Example 1 and Comparative Example 1 in shorter columns (φ4.6 X 35 mm). The packing method was the same as in Example 1.

By using the separation columns of Example 2 and Comparative Example 2, glycohemoglobin and hemoglobin were measured. The same system as in Example 1 was used. The same sample as in Example 1 was used again. The separation of the individual components was according to the step-wise gradient method as shown hereinafter. The compositions of eluents A, B, and C solutions are the same as in Example 1, but the gradient program and the flow of the eluents are different from those in Example 1.

| | |
|---|---|
| First solution: A solution | 0–0.2 min |
| Second solution: B solution | 0.3–1.5 min |
| Third solution: C solution | 1.6–1.9 min |
| Fourth solution: A solution | 2.0–3.5 min |
| Flow of eluent: 1.4 ml/min | |

TABLE 2

| | Column size | Particle diameter (μm) | Specific surface area (m$^2$/g) |
|---|---|---|---|
| Example 2 | φ 4.6 X 35 mm | 4.5 ± 0.8 | 20 |
| Comparative Example 2 | φ 4.6 X 35 mm | 4.5 ± 0.8 | 18 |
| | Carboxymethyl group (meq/g) | Dihydroxymethyl group (meq/g) | Pressure loss P 1) (kg/cm$^2$) |
| Example 2 | 0.30 | 0.18 | 48 |
| Comparative Example 2 | 0.28 | — | 47 |

1) Flow of eluent: 1.4 ml/min

Figure 3:
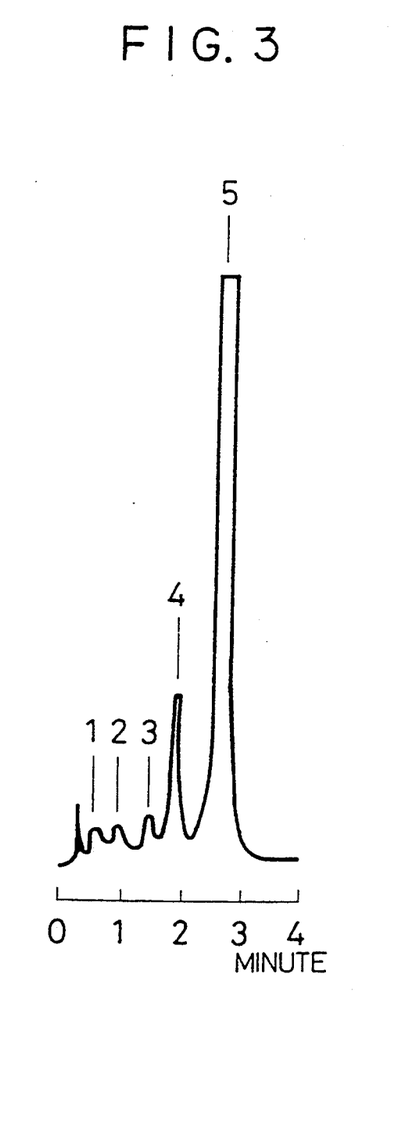
FIG. 3 shows the chromatogram obtained in Example 2.
Figure 4:
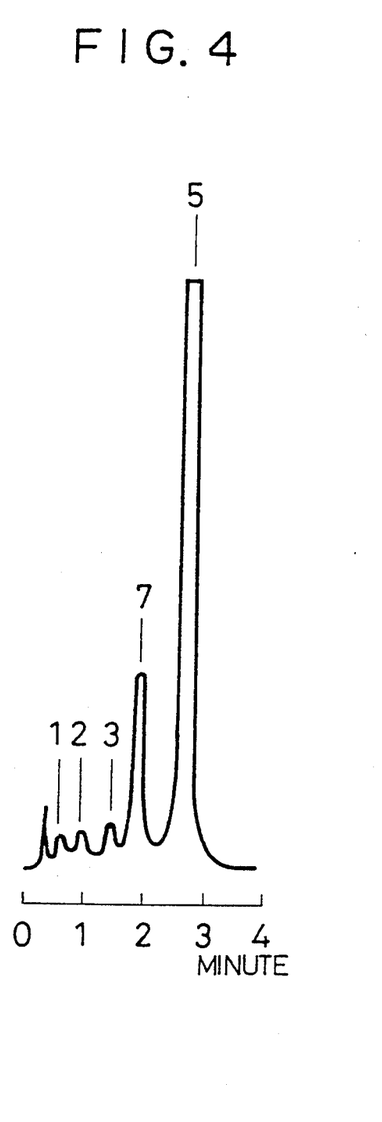
FIG. 4 shows the chromatogram obtained in Comparative Example 2.

Under the analytical conditions described hereinabove, the chromatogram obtained on the separation column of Example 2 and the chromatogram obtained on the separation column of Comparative Example 2 are shown in FIGS. 3 and 4, respectively. The pressure losses of the columns at an eluent flow of 1.4 ml/min, in Example 2 and Comparative Example 2, were 48 kg/cm$^2$ and 47 kg/cm$^2$, respectively.

In FIG. 3, Peak 1 represents $A_{1a}$; Peak 2, $A_{1b}$; Peak 3, HbF; Peak 4, s-$A_{1c}$; Peak 5, HbA$_0$. In FIG. 4, Peak 1 represents $A_{1a}$; Peak 2, $A_{1b}$; Peak 3, HbF; Peak 7, {(l-$A_{1c}$)+(s-$A_{1c}$)}; Peak 7, HbA$_0$.

In FIGS. 3 and 4, the retention times of the individual components are nearly equal. The retention time of Peak 4 (s-$A_{1c}$) in FIG. 3 is equal to the retention time of Peak 7 {(l-$A_{1c}$)+(s-$A_{1c}$)}. The peak area of Peak 7 is larger by about 10% than the peak area of Peak 4. The retention time of Peak 7 in FIG. 4 is equal to the retention time of Peak 4 in FIG. 3. However, it is considered that because Peak 7 contains l-$A_{1c}$, the peak area is larger for that part.

The chromatograms of 60 samples were analyzed by the methods of Example 2 and Comparative Example 2. The area of Peak 4 (s-$A_{1c}$) was compared with the area of Peak 7 {(l-$A_{1c}$)+(s-$A_{1c}$)}. The area of Peak 7 was larger by 6.8% on average (range between 3 and 12%) than that of Peak 4. The value of glycohemoglobin in hunger was measured, It is considered that the proportion of l-$A_{1c}$ gets larger immediately after meal.

In Example 2 (FIG. 3), l-$A_{1c}$ is decomposed inside the separation column, so that five components of $A_{1a}$, $A_{1b}$, HbF, s-$A_{1c}$ and HbA$_0$ can be separated from each other for just 3.5 minutes. Thus, s-$A_{1c}$ can be measured. In case that l-$A_{1c}$ and s-$A_{1c}$ are separated from each other by chromatography as in Comparative Example 1 (FIG. 2), alternatively, a longer column should be necessarily used compared with the column of Example 2 if identical fillers are used, resulting in a longer analysis time for that part. Apparently from FIG. 2, the time required for the measurement of one sample is seven minutes, requiring the two-fold time that of Example 2 (FIG. 3).

According to the present Example, as has been described above, s-$A_{1c}$ can be measured for a shorter time, compared with the chromatographic method of separating s-$A_{1c}$ from l-$A_{1c}$. Because the amount of fillers to be packed is less as the length of columns gets shorter, the columns cost less. Furthermore, the amount of an eluent to be used gets less, leading to the reduction of the running cost.

Comparison was effected between the measured values of Example 2 and the measured values of Comparative Example 1.

Figure 5:
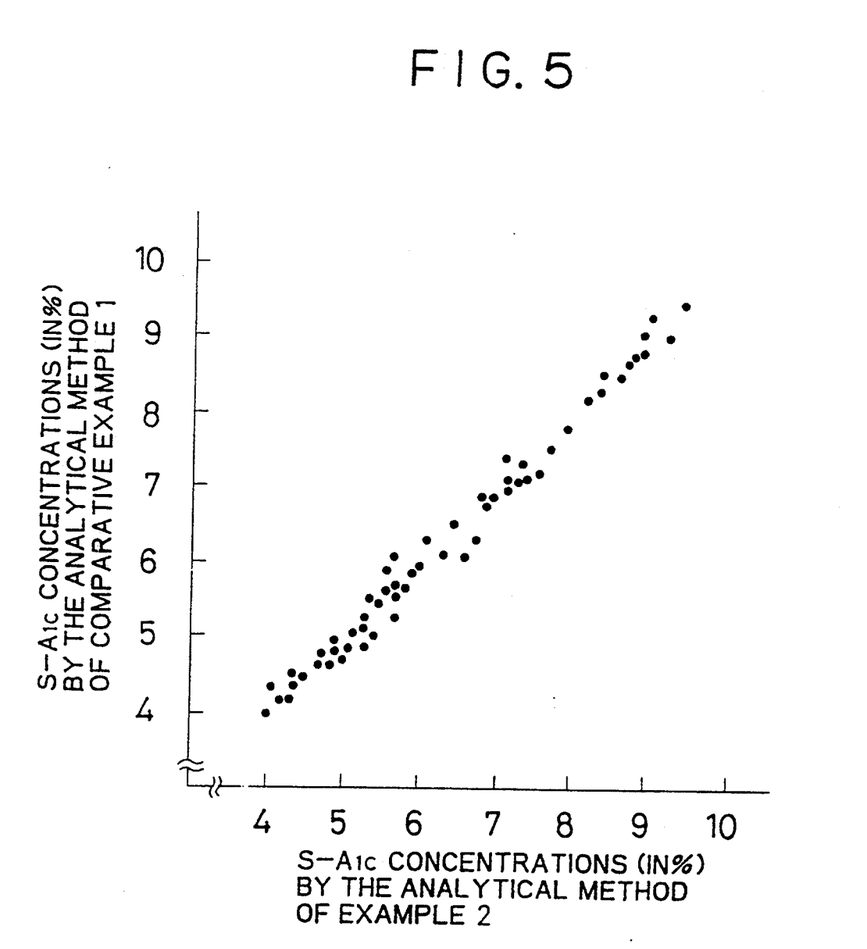
FIG. 5 is a figure representing the correlation between the stable-type $A_{1c}$ (s-$A_{1c}$) levels measured by the method of Example 2 and the s-$A_{1c}$ levels measured by the method of Comparative Example 1.

As samples, there was used anti-coagulant-containing fresh blood from healthy adults or diabetic patients, which was preliminarily diluted with a hemolytic agent. The results of 60 samples measured are shown in FIG. 5. The axis of abscissas of the figure represents the s-$A_{1c}$ concentrations (in %) measured by the method of Example 2, while the axis of ordinates represents the s-$A_{1c}$ measured by the method of Comparative Example 1.

The coefficient of correlation, $\gamma$, between the method of Example 2 and that of Comparative Example 1, was 0.992. The correlation formula is represented by $Y = 1.03 - 0.31$ wherein the s-$A_{1c}$ concentration obtained by the method of Example 2 is represented by X and the s-$A_{1c}$ concentration obtained by the method of Comparative Example 1 is represented by Y. Thus, an extremely good correlation was obtained between the two methods.

As has been described above, the method of Example 2 can be regarded as a method capable of analyzing stable-type $A_{1c}$ (s-$A_{1c}$) in blood, rapidly and with good reproducibility.

EXAMPLE 3

Figure 6:
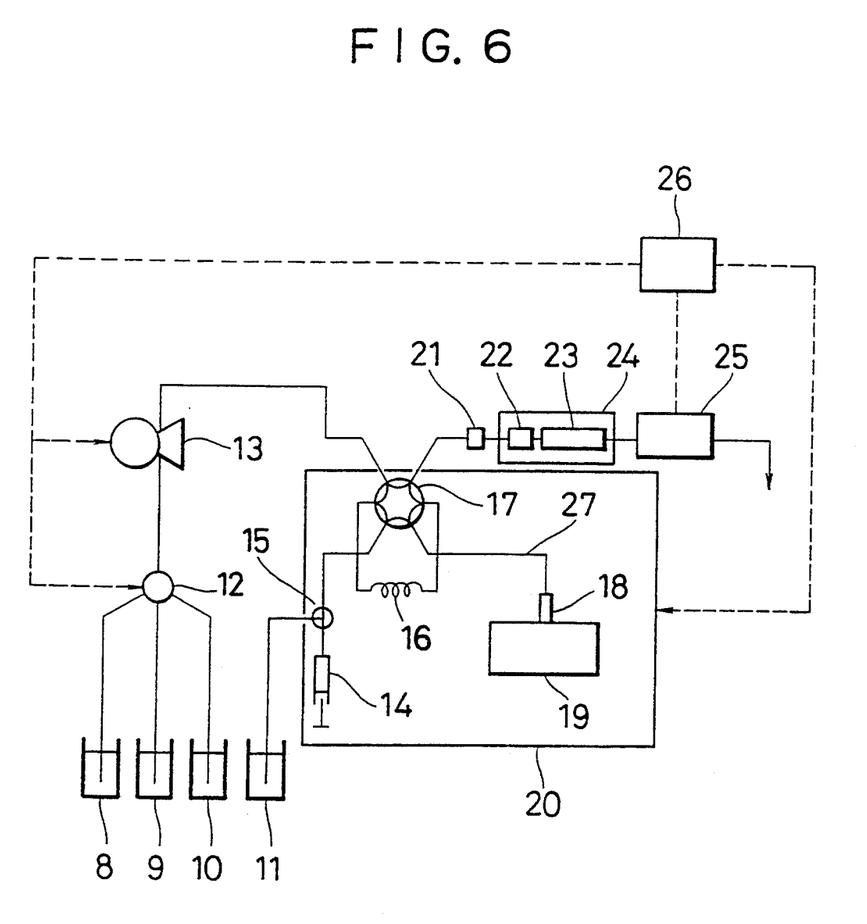
FIG. 6 is one embodiment of the analytical apparatus of the present invention.

FIG. 6 represents one example of the separation system of glycohemoglobin, in accordance with the present invention.

As samples, fresh blood collected after the addition of sodium ethylenediamine tetraacetate salt as an anti-coagulant was used. The blood was diluted 200-fold with a commercially available hemolytic agent, and the diluted blood was mounted on sample table 19 of autosampler 20.

As separation column 23, there was used the same one as used in Comparative Example 2. The column size was an inner diameter of 4.6 mm and a length of 35 mm. As a filler, there was used the one wherein carboxymethyl group was introduced into methacrylate gel of a particle diameter of 4.5 μm. In pretreatment column 22 as a column for removing l-$A_{1c}$, there was used a filler of a particle diameter of 8 μm wherein dihydroxyboronyl group was introduced into methacrylate gel. The size of the pretreatment column was an inner diameter of 4.6 mm and a length of 10 mm. In case that the column, which was employed in Example 2 and wherein carboxymethyl group and dihydroxyboronyl group were introduced into methacrylate gel and the particle size is 4.5 μm, is to be used, the removal of l-$A_{1c}$ and the separation of Hb into its individual components are carried out on the single column, so that pretreatment column 22 is not necessary. The temperature of column thermostat 24 was preset at 30° C. As eluents, First solution 8, Second solution 9 and Third solution 10 were used, as shown in Example 2.

In FIG. 6, the arrow in solid line represents the flow of liquids of samples or eluents, while the arrow in dotted line represents the flow of signals.

The separation of the individual components were carried out following the step-wise gradient method.

| | |
|---|---|
| First solution: A solution | 0–0.2 min |
| Second solution: B solution | 0.3–1.5 min |
| Third solution: C solution | 1.6–1.9 min |
| First solution: A solution | 2.0–3.5 min |
| Flow of eluent: 1.4 ml/min | |

The sample mounted on sample table 19 is transferred through aspiration nozzle 18 and sample transferring pipe 27 into sample loop 16 by means of syringe 14, and then it is measured. Washing solution 11 is fed through three way valve 15. By switching six way valve 17, the sample measured in sample loop 16 is passed through filter 21 and is transferred to pretreatment column 22, and then it is continuously charged into separation column 23.

After passed through three way electric valve 12 by means of transferring pump 13 and transferred through filter 21 to pretreatment column 22, eluents First solution 8, Second solution 9, Third solution 10 are fed into separation column 23. By UV-VIS detector 25, the absorbance of the eluate from separation column 23 was measured at a wave length of 415 nm; the absorbance at a wave length of 690 nm was also measured for reference.

Under the gradient conditions, the chromatogram as shown in FIG. 3 can be obtained. That is, as shown in FIG. 3, hemoglobin can be separated into $A_{1a}$, $A_{1b}$, HbF, s-$A_{1c}$ and HbA$_0$ at one cycle of just 3.5 minutes. The ratio of s-$A_{1c}$ (in percentage) to total Hb was determined based on the chromatograms, by means of data processor 26 (data processing unit).

Because the removal of l-$A_{1c}$ can be continuously effected within the system according to the present invention, automatization of such procedure can be easily achieved. As l-$A_{1c}$ can be automatically removed, the precision in measurement is good; in other words, the reproducibility of measured values is good. Furthermore, the procedure is simple.

Figure 7:
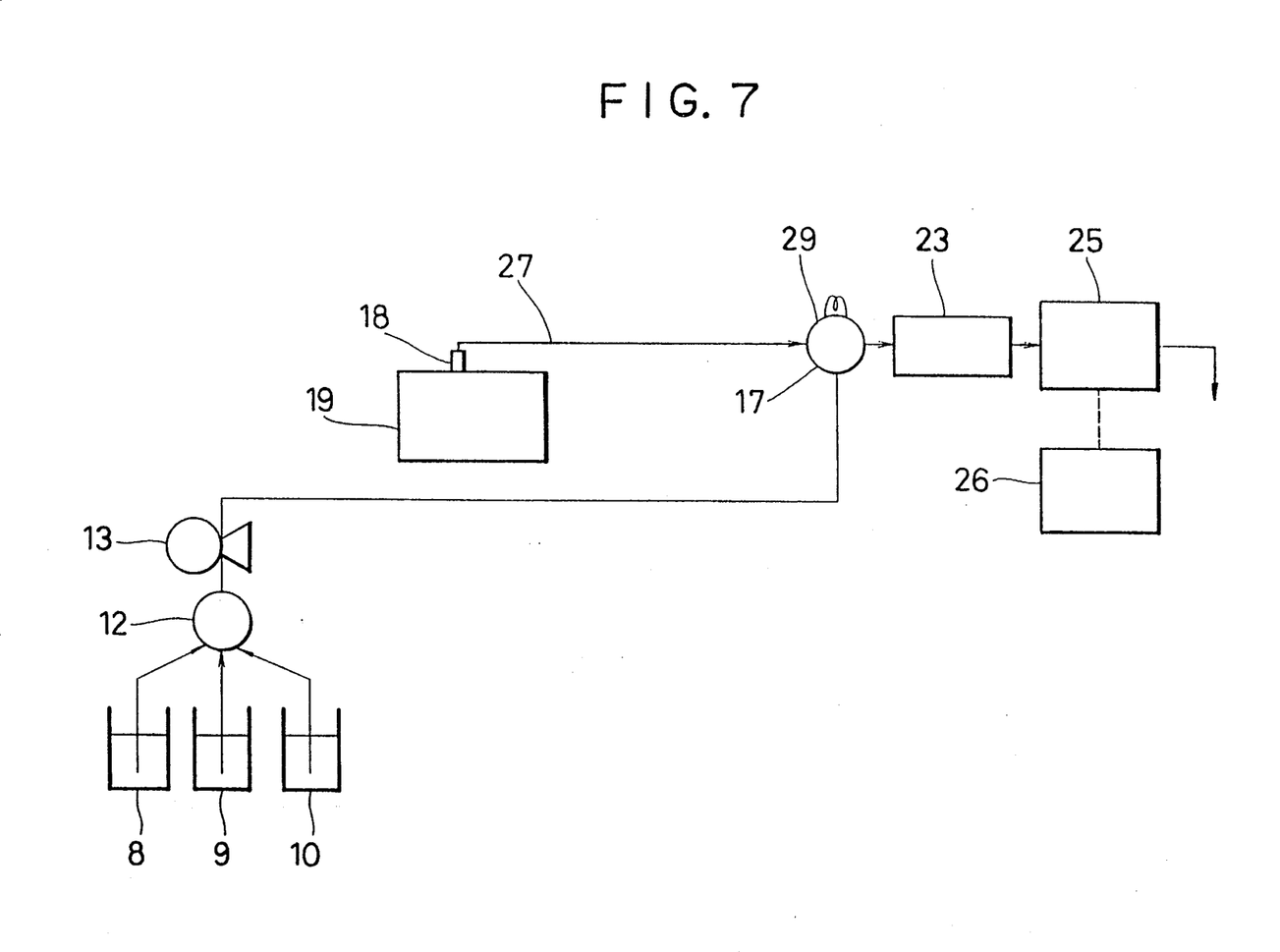
FIG. 7 is a construction figure of the elemental parts of the separation apparatus of the present invention.
Figure 8:
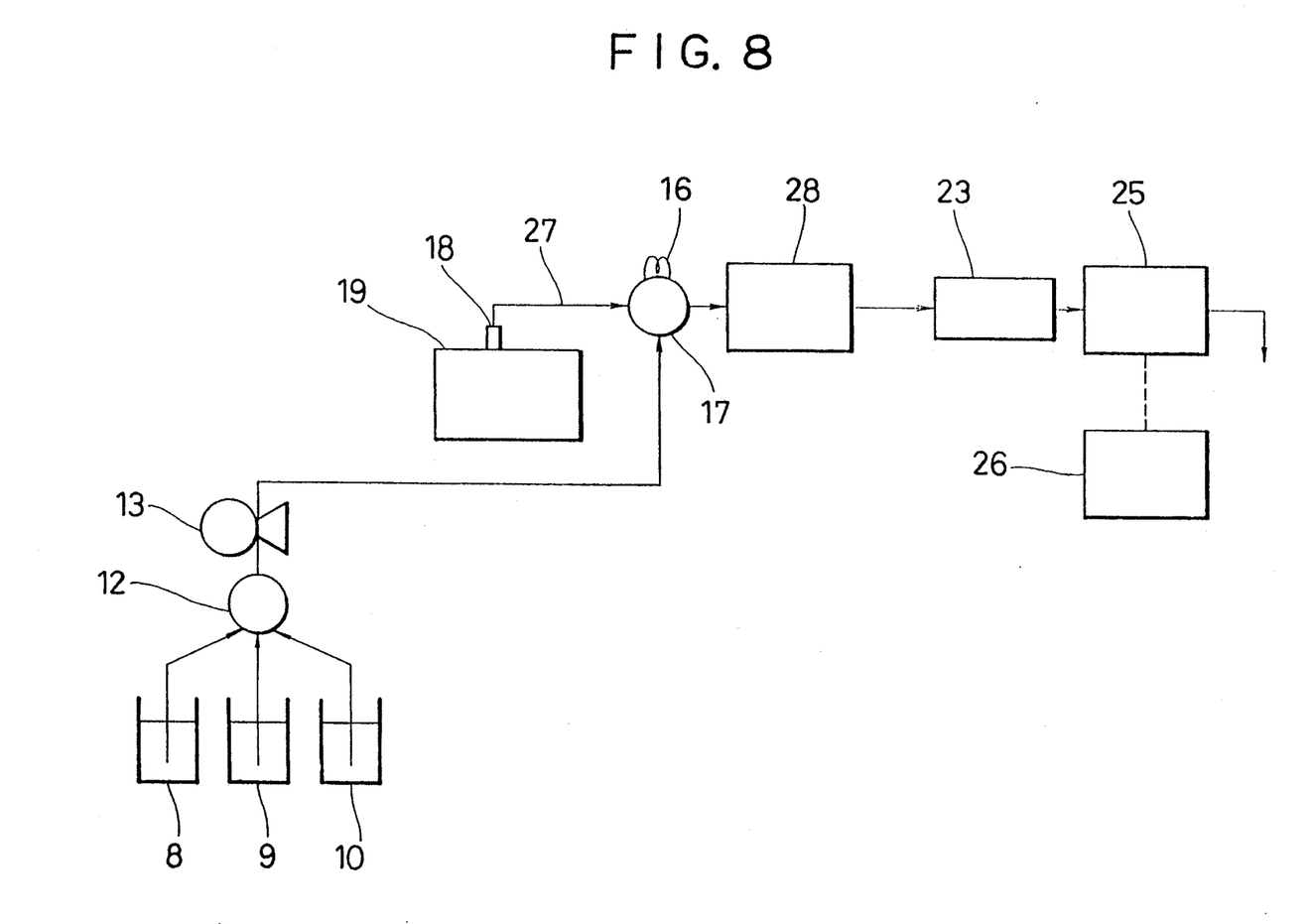
FIG. 8 is a construction figure of the elemental parts of the separation apparatus of the Comparative Example 3.

The main system construction of the apparatus of the present invention is depicted in FIG. 7, while one embodiment of the system construction of the apparatus of Comparative Example 3 is depicted in FIG. 3. As depicted in FIG. 8, the sample preset on sample table 19 of the autosampler is measured through sample transferring pipe 27 in sample loop 16, and the sample is introduced into l-$A_{1c}$ removing part 28 by switching six way valve 17. The l-$A_{1c}$ in blood is removed or reduced at l-$A_{1c}$ removing part 28 by heat treatment and the like. The sample from which l-$A_{1c}$ is removed is introduced into separation column 23. On the other hand, eluents 8 and 9 are fed through three way electromagnetic valve 12 into separation column 23 by means of transferring pump 13. The eluate from separation column 23 is detected by UV-VIS detector 25. As has been described above, the filler packed in the separation column of Comparative Example 3 is an ion exchange resin wherein carboxyl group is introduced into, for example, silica gel and methacrylate gel. Thus, it does not have an action of removing l-$A_{1c}$, so that a part for removing l-$A_{1c}$ should be placed prior to the injection part of the column. On the contrary, the separation column of the present invention has the following two actions, i.e. the separation of hemoglobin and glycohemoglobin and the removal of l-$A_{1c}$. As shown in FIG. 7, the positioning of an l-$A_{1c}$ removing mechanism is not required. Hence, the apparatus of the present invention is simpler in its system construction and can be designed in a smaller scale.

As separation column 23, one of the three types described hereinafter is mounted, namely, 1. separation column packed with a filler consisting of an inorganic or organic porous substance having carboxyalkyl group and dihydroxyboronyl group; 2. separation column packed with a filler produced by mixing a filler consisting of an inorganic or organic porous substance having carboxyalkyl group with a filler consisting of an inorganic or organic porous substance having dihydroxyboronyl group; and 3. separation column wherein a filler consisting of an inorganic or organic porous substance having carboxyalkyl group and a filler consisting of an inorganic or organic porous substance having dihydroxyboronyl group are packed separately in two layers in the flow direction of eluents. The fillers inside the separation column are specified such that the specific surface area is 5 to 200 $m^2$/g in a dry state, that the amount of carboxyalkyl group is 0.1 to 1 meq per g.dry weight, and that the amount of dihydroxyboronyl group is 0.1 to 1 meq per g.dry weight.

According to the present invention, the removal of l-$A_{1c}$ and the separation of Hb into its individual components can be carried out on an identical separation column or continuously within the system, so that the time period required for the decomposition of l-$A_{1c}$, which has conventionally required a long time i.e. 15 minutes to four hours, can be shortened.

Because the complex procedure so as to remove l-$A_{1c}$ cannot be necessarily done, the procedure can be extremely simplified also.

Because the decomposition of l-$A_{1c}$ does not involve the degeneration of GHb and Hb, accurately measured values of s-$A_{1c}$ can be obtained as well.

Because l-$A_{1c}$ can be removed continuously within the system, automatization of the procedure can be easily realized, whereby the precision in measurement and the reproducibility of measured values can be improved.

We claim:

1. An apparatus for measuring glycohemoglobin to measure stable-type hemoglobin by high performance liquid chromatography, comprising a separation column for separating glycohemoglobin in blood, a means for injecting a diluted blood sample into the separation column, a means for passing eluents into the separation column and a means for detecting stable-type hemoglobin in an eluate from the separation column, wherein the separation column is provided with filler means having carboxyalkyl groups and dihydroxyboronyl groups for simultaneously carrying out the procedure of separating glycohemoglobin, hemoglobin and hemoglobin derivatives and the procedure of decomposing labile-type hemoglobin in the blood into glucose and hemoglobin so as to remove the labile-type hemoglobin.

2. An apparatus for measuring glycohemoglobin to measure stable-type hemoglobin by high-performance liquid chromatography, comprising a separation column for separating glycohemoglobin in blood, a means for injecting a diluted blood sample into the separation column, a means for passing eluents into the separation column and a means for detecting stable-type hemoglobin in an eluate from the separation column, wherein the separation column is packed with a filler consisting of an inorganic or organic porous substance having carboxyalkyl group and dihydroxyboronyl group.

3. An apparatus for measuring glycohemoglobin to measure stable-type hemoglobin by high-performance liquid chromatography, comprising a separation column for separating glycohemoglobin in blood, a means for injecting a diluted blood sample into the separation column, a means for passing eluents into the separation column and a means for detecting stable-type hemoglobin in an eluate from the separation column, wherein the separation column is packed with a filler produced by mixing a filler consisting of an inorganic or organic porous substance having carboxyalkyl group and a filler consisting of an inorganic or organic porous substance having dihydroxyboronyl group.

4. An apparatus for measuring glycohemoglobin to measure stable-type hemoglobin in blood by high-performance liquid chromatography, comprising a separation column for separating glycohemoglobin in blood, a means for injecting a diluted blood sample into the separation column, a means for passing eluents into the separation column and a means for detecting stable-type hemoglobin in an eluate from the separation column, wherein a filler consisting of an inorganic or organic porous substance having carboxyalkyl group and a filler consisting of an inorganic or organic porous substance having dihydroxyboronyl group are separated in two layers and packed individually in the separation column.

5. An apparatus for measuring glycohemoglobin to measure stable-type hemoglobin by high-performance liquid chromatography, comprising a separation column for separating glycohemoglobin in blood, a means for injecting a diluted blood sample into the separation column, a means for passing eluents into the separation column and a means for detecting stable-type hemoglobin in an eluate from the separation column, wherein the separation column is divided in two parts in the flow direction of eluents, one part being packed with a filler consisting of an inorganic or organic porous substance having carboxyalkyl group and the other part being packed with a filler consisting of an inorganic or organic substance having dihydroxyboronyl group.

6. An apparatus for measuring glycohemoglobin to measure stable-type hemoglobin by high-performance liquid chromatography, comprising a separation column for separating glycohemoglobin in blood, a means for injecting a diluted blood sample into the separation column, a means for passing eluents into the separation column and a means for detecting stable-type hemoglobin in an eluate from the separation column, wherein the separation column is divided with filler means for simultaneously carrying out the procedure of separating glycohemoglobin, hemoglobin and hemoglobin derivatives and the procedure of decomposing labile-type hemoglobin in the blood into glucose and hemoglobin so as to remove the labile-type hemoglobin.

* * * * *